United States Patent [19]

Kasturi et al.

[11] Patent Number: 5,707,950
[45] Date of Patent: Jan. 13, 1998

[54] DETERGENT COMPOSITIONS CONTAINING LIPASE AND PROTEASE

[75] Inventors: Chandrika Kasturi, Fairfield, Ohio; Andre Baeck, Bonheiden, Belgium; Ann Margaret Wolff, Cincinnati, Ohio

[73] Assignee: The Procter & Gamble Company, Cincinnati, Ohio

[21] Appl. No.: 729,543

[22] Filed: Oct. 11, 1996

Related U.S. Application Data

[63] Continuation of Ser. No. 341,828, Nov. 18, 1994, abandoned.

[51] Int. Cl.⁶ ..................................... C11D 3/386
[52] U.S. Cl. .................. 510/320; 510/392; 510/530; 8/137
[58] Field of Search ..................... 435/219–225, 435/198, 263, 264; 510/320, 392, 530; 8/137

[56] References Cited

U.S. PATENT DOCUMENTS

| | | | |
|---|---|---|---|
| 4,769,173 | 9/1988 | Cornelissen et al. | 252/174 |
| 4,810,414 | 3/1989 | Hse-Jensens | 252/174.12 |
| 5,069,809 | 12/1991 | Lagerwaard et al. | 252/174.12 |
| 5,078,898 | 1/1992 | Jars | 252/174.12 |
| 5,100,796 | 3/1992 | Paridans et al. | 435/198 |
| 5,185,250 | 2/1993 | Brenner et al. | 435/69.3 |
| 5,204,015 | 4/1993 | Caldwell et al. | 252/174.12 |
| 5,520,835 | 5/1996 | Siuik et al. | 510/220 |
| 5,559,089 | 9/1996 | Hartman et al. | 510/224 |

FOREIGN PATENT DOCUMENTS

| | | | |
|---|---|---|---|
| 218272 | 4/1987 | European Pat. Off. | C11D 3/386 |
| 271154 | 6/1988 | European Pat. Off. | |
| 381397 | 8/1990 | European Pat. Off. | C11D 3/386 |
| 405901 | 1/1991 | European Pat. Off. | C11D 3/386 |
| 0516200 | 12/1992 | European Pat. Off. | |
| 9205249 | 4/1992 | WIPO | |
| WO 92/05249 | 4/1992 | WIPO | C12N 9/20 |
| 9211348 | 7/1992 | WIPO | |
| 9218599 | 10/1992 | WIPO | |
| WO 93/23516 | 11/1993 | WIPO | C11D 3/386 |
| WO 94/03578 | 2/1994 | WIPO | C11D 3/386 |
| WO 94/10284 | 5/1994 | WIPO | C11D 3/386 |
| WO 95/10591 | 4/1995 | WIPO | C11D 3/386 |

OTHER PUBLICATIONS

U.S. application No. 08/341826, Baeck et al. filed Nov., 18, 1994.

Malmos, Gormsen, "A New Lipase for the Detergent Industry", HAPPI (Household & Personal Products Industry), vol. 28, No. 10, Oct. 1991, pp. 122–125.

Research Disclosure No. 35944 by NOVO, Mar. 10, 1994.

Research Disclosure, vol. 2244, No. 359, Mar. 1994 "Detergent Compositions Comprising Lipase Variants", pp. 151–156.

*Primary Examiner*—Paul Lieberman
*Assistant Examiner*—Kery A. Fries
*Attorney, Agent, or Firm*—K. W. Zerby; J. J. Yetter; J. C. Rasser

[57] ABSTRACT

The invention concerns laundry detergent compositions comprising lipase (especially the variant D96L of the native lipase derived from *Humicola lanuginosa*), protease, and surfactant, wherein said compositions comprise levels of lipase enzyme and protease enzyme such that the whitening performance of said compositions is increased. These compositions deliver an improved whiteness maintenance and/or dingy clean-up on fabrics.

2 Claims, No Drawings

DETERGENT COMPOSITIONS CONTAINING LIPASE AND PROTEASE

This is a continuation of application Ser. No. 08/341,828, filed on Nov. 18, 1994 abandoned.

FIELD OF THE INVENTION

The present invention relates to laundry detergent compositions containing lipolytic enzyme, proteolytic enzyme, and surfactant, and the use of said compositions in laundry cleaning processes to provide whiteness maintenance and/or dingy clean-up.

BACKGROUND OF THE INVENTION

The inclusion of lipase in detergent compositions for improved cleaning performance is known, e.g. enhancement of removal of triglycerides containing soils and stains from fabrics. Examples are U.S. Pat. No. 4,769,173, Cornelissen et al. issued Aug. 29, 1989; U.S. Pat. No. 5,069,809, Lagerwaard et at., issued Dec. 3, 1991; PCT application WO94/03578 and HAPPI (Household & Personal Products Industry) No. 28/1991.

In U.S. Pat. No. 4,769,173 is disclosed a certain class of lipases consisting of fungal lipases ex *Humicola lanuginosa* together with strong bleaching agents in detergent compositions. An example of a fungal lipase in this patent is the lipase ex *Humicola lanuginosa*, available from Amano under the tradename Amano-CE.

In U.S. Pat. No. 5,069,809 is disclosed the combination of strong bleaching agents with a lipase enzyme produced by cloning the gene encoding the lipase produced by *Humicola lanuginosa* and expressing the gene in *Aspergillus oryzae* as host for use in detergent compositions.

In WO 94/03578 is disclosed an enzymatic detergent composition containing 10 to 20 000 LU (Lipolytic units) per gram of detergent composition of a lipase showing a substantial lipolytic activity during the main cycle of a wash process. This lipase is selected in particular on its inactivation behaviour with Diisopropyl Fluoro Phosphate (DFP).

Likewise, the inclusion of proteases in detergent compositions for improved cleaning performance is known. For example, protease enzymes are described in U.S. Pat. No. 5,185,250 and U.S. Pat. No. 5,204,015. In addition, bleach compositions containing protease having enhanced stain removal properties are also known, having been described in WO 94/10284, published May 11, 1994, by The Procter & Gamble Company. Commercially available protease enzymes include Alcalase®, Esperase®, Durazym®, Savinase®, Maxtase®, Maxacal®, and Maxapem® 15 (protein engineered Maxacal); Purafect® and subtilisin BPN and BPN'.

Of the lipase enzymes, only the lipase derived from *Humicola lanuginosa* and produced in *Aspergillus oryzae* as host has so far found wide-spread application as additive for fabric washing products. It is available under the tradename Lipolase®, from Novo Nordisk. Gormsen and Malmos describe in HAPPI Lipolase as being the first detergent lipase with a commercially relevant cost performance based on the use of recombinant DNA technology on an industrial scale.

In order to optimize the stain removal performance of Lipolase, Novo Nordisk have made a number of variants. WO 92/05249 describes the D96L variant of the native *Humicola lanuginosa* lipase improves the lard stain removal efficiency by a factor 4.4 over the wild-type lipase (enzymes compared in an amount ranging from 0.075 to 2.5 mg protein per liter). Example 20 therein describes the storage stability of certain of these lipases in liquid detergent compositions in the presence of the protease Alcalase®.

Research Disclosure No. 35944 published on Mar. 10, 1994, by Novo Nordisk discloses that the lipase variant (D96L) may be added in an amount corresponding to 0.001–100 mg lipase variant per liter of wash liquor. The compositions therein are said to optionally comprise "one or more other enzymes, such as amylase, cutinase, protease, cellulase, peroxidase, and oxidase."

Finally, detergent compositions comprising combinations of Lipolase and certain proteases are commercially known, for example in the U.S. Tide® and in Europe Ariel® (both brands sold by The Procter & Gamble Company).

However, the benefits of whiteness maintenance and dingy clean-up on fabrics using combinations of lipase and protease, preferably low levels of D96L lipase variant in detergent compositions, has not been previously recognized.

It has been found that lipase enzymes can be combined with protease enzymes in surfactant compositions to obtain surprisingly effective dingy soil clean-up and/or whiteness maintenance benefits. Accordingly, it is an object of the present invention to provide improved laundry cleaning compositions using lipase enzymes, protease enzymes and surfactants. It is another object herein to provide a means for removing dingy soils from fabrics using laundry compositions containing lipase, protease, and surfactant. It is a further object to provide a means for maintaining whiteness of fabrics using laundry compositions containing lipase, protease, and surfactant. These and other objects are secured herein, as will be seen from the following disclosures.

SUMMARY OF THE INVENTION

The present invention relates to laundry detergent compositions comprising: (a) a lipase enzyme other than Lipolase; (b) a protease enzyme other than Alcalase®; and (c) a surfactant; and wherein further said compositions comprise levels of lipase enzyme and protease enzyme such that the whitening performance of said compositions is increased.

Preferred are solid (preferably granular) laundry detergent compositions comprising: (a) a lipase enzyme variant D96L of the native lipase derived from *Humicola lanuginosa*; (b) a protease enzyme; and (c) a surfactant; and wherein further said compositions comprise levels of said lipase enzyme and protease enzyme such that the whitening performance of said compositions is increased.

Also preferred are laundry detergent compositions comprising: (a) a lipase enzyme (preferably Lipolase and/or a lipase enzyme variant D96L of the native lipase derived from *Humicola lanuginosa*); (b) a protease enzyme which is derived from a precursor carbonyl hydrolase by substituting a different amino acid for the amino acid residue at position in said carbonyl hydrolase equivalent to position +76 (preferably in combination with one or more amino acid residue positions equivalent to those selected from the group consisting of+99, +101, +103, +104, +107, +123, +27, +105, +109, +126, +128, +135, +156, +166, +195, +197, +204, +206, +210, +216, +217, +218, +222, +260, +265, and/or +274) according to the numbering of *Bacillus amyloliquefaciens* subtilisin; and (c) a surfactant; and wherein further said compositions comprise levels of lipase enzyme and protease enzyme such that the whitening performance of said compositions is increased.

The preferred lipolytic enzyme variant D96L of native *Humicola lanuginosa* lipase is preferably incorporated into detergent compositions at a level of from 50 lipolytic units (LU) to 8500 LU per liter wash solution.

Finally, the present invention relates to methods for laundering fabrics to maintain whiteness and provide dingy cleanup, said methods comprising contacting fabrics in need of whiteness and dingy clean-up with an aqueous solution of a composition comprising lipase enzyme and protease enzyme at levels such that the whitening performance of said composition is increased.

All percentages, ratios and proportions herein are by weight, unless otherwise specified. All documents cited are, in relevant part, incorporated herein by reference.

DETAILED DESCRIPTION OF THE INVENTION

Without limitation by theory, it is believed that dingy soils are the result of combinations of fatty soils and particulate soils. Fatty soils comprise lipids, proteins, and pigments that are deposited over time on fabrics from contact with human or animal skin. The majority of lipids are secreted from the sebaceous gland as sebum. Proteins and pigments from skin fragments are liberated by the breakdown of skin cells. Particulate soils comprise mostly airborne soil and floor/ground dust. It is believed that sebum is the major soil present on laundry, and its removal is important because unremoved fat acts as a matrix to hold particulate soils. Further it is believed that compounds present in the sebum can oxidize to contribute to yellowing of fabrics. Particulate soils include topsoil and products produced during the incomplete combustion of petroleum products. "Dingy clean-up", as used herein, means the ability of a detergent composition to remove such dingy soil build-up, over one or more washes, resulting in a measurable improvement in fabric appearance.

Whiteness maintenance is the monitoring of the whiteness of wash & wear fabrics over a number of washing cycles. A good performing detergent has a good whiteness maintenance profile, i.e. it ensures that the whiteness of washed fabrics is maintained at a high level during the complete life cycle of wearing & washing.

"Whitening performance", as used herein, means the relative ability of laundry detergent compositions comprising both lipase and protease enzymes (as compared versus the same compositions comprising only protease enzyme or lipase enzyme, under whatever comparative test conditions are employed) to produce dingy clean-up and/or whiteness maintenance results.

Lipase Enzymes:

Lipase enzymes which may be considered for inclusion in the detergent compositions of the present invention include those produced by microorganisms of the Pseudomonas group, such as Pseudomonas stutzeri ATCC 19.154, as disclosed in British Patent 1,372,034. Lipases include those which show a positive immunological cross-reaction with the antibody of the lipase, produced by the microorganism Pseudomonas fluorescens IAM 1057. This lipase is available from Amano Pharmaceutical Co. Ltd., Nagoya, Japan, under the trade name Lipase P "Amano," hereinafter referred to as "Amano-P". Lipases include M1 Lipase$^R$ and Lipomax$^R$ (Gist-Brocades) and Lipolase$^R$ (Novo).

The lipases are normally incorporated in the detergent composition at levels from 0.0001% to 2% of active enzyme by weight of the detergent composition.

A preferred component of the detergent composition according to the invention is the D96L lipolytic enzyme variant of the native lipase derived from Humicola lanuginosa. Preferably the Humicola lanuginosa strain DSM 4106 is used. This enzyme is preferably incorporated into the composition in accordance with the invention at a level of from about 50 LU to about 8500 LU per liter wash solution. More preferably the variant D96L is present at a level of from about 100 LU to about 7500 LU per liter of wash solution, and most preferably at a level of flora about 150 LU to about 5000 LU per liter of wash solution.

By D96L lipolytic enzyme variant is meant the lipase variant as described in patent application WO 92/05249 viz. wherein the native lipase ex Humicola lanuginosa aspartic acid (D) residue at position 96 is changed to Leucine (L). According to this nomenclature said substitution of aspartic acid to Leucine in position 96 is shown as: D96L.

To determine the activity of the enzyme D96L the standard LU assay was used (Analytical method, internal Novo Nordisk number AF 95/6-GB 1991.02.07). A substrate for D96L was prepared by emulsifying glycerine tributyrat (Merck) using gum-arabic as emulsifier. Lipase activity was assayed at pH 7 using pH stat. method. One unit of lipase activity (LU/mg) is defined as the amount needed to liberate one micromole fatty acid per minute.

The D96L variant of the native Humicola lanuginosa lipase has the additional advantage of delivering a significant benefit in whiteness maintenance when compared to the wildtype lipase.

Protease Enzymes

Protease enzymes are usually present at levels sufficient to provide from 0.005 to 0.1 Anson units (AU) of activity per gram of composition. The proteolytic enzyme can be of animal, vegetable or microorganism (preferred) origin. More preferred is serine proteolytic enzyme of bacterial origin. Purified or nonpurified forms of enzyme may be used. Proteolytic enzymes produced by chemically or genetically modified mutants are included by definition, as are close structural enzyme variants. Particularly preferred by way of proteolytic enzyme is bacterial serine proteolytic enzyme obtained from Bacillus, Bacillus subtilis and/or Bacillus licheniformis. Suitable commercial proteolytic enzymes which may be considered for inclusion in the present invention compositions include Alcalase®, Esperase®, Durazym®, Savinase®, Maxatase®, Maxacal®, and Maxapem® 15 (protein engineered Maxacal); Purafect® and subtilisin BPN and BPN'.

Proteolytic enzymes also encompass modified bacterial serine proteases, such as those described in European Patent Application Serial Number 87 303761.8, filed Apr. 28, 1987 (particularly pages 17, 24 and 98), and which is called herein "Protease B", and in European Patent Application 199,404, Venegas, published Oct. 29, 1986, which refers to a modified bacterial serine proteolytic enzyme which is called "Protease A" herein. More preferred is what is called herein "Protease C", which is a variant of an alkaline serine protease from Bacillus in which lysine replaced arginine at position 27, tyrosine replaced valine at position 104, serine replaced asparagine at position 123, and alanine replaced threonine at position 274. Protease C is described in EP 90915958:4, corresponding to WO 91/06637, Published May 16, 1991, which is incorporated herein by reference. Genetically modified variants, particularly of Protease C, are also included herein.

Preferred proteolytic enzymes are selected from the group consisting of Savinase®, Esperase®, Maxacal®, Purafect®, BPN', Protease A and Protease B, and mixtures thereof. Bacterial serine protease enzymes obtained from Bacillus subtilis and/or Bacillus licheniformis are preferred.

An especially preferred protease herein referred to as "Protease D" is a carbonyl hydrolase variant having an amino acid sequence not found in nature, which is derived from a precursor carbonyl hydrolase by substituting a different amino acid for the amino acid residue at a position in said carbonyl hydrolase equivalent to position +76, preferably also in combination with one or more amino acid residue positions equivalent to those selected from the group consisting of +99, +101, +103, +104, +107, +123, +27, +105, +109, +126, +128, +135, +156, +166, +195, +197, +204, +206, +210, +216, +217, +218, +222, +260, +265, and/or +274 according to the numbering of *Bacillus amyloliquefaciens* subtilisin, as described in the concurrently filed patent application of A. Baeck et at. entitled "Protease-Containing Cleaning Compositions" having U.S. Ser. No. 08/322,676, filed Oct. 13, 1994, which is incorporated herein by reference in its entirety.

Surfactants

The detergent compositions according to the present invention comprise a surfactant system wherein the surfactant can be selected from nonionic and/or anionic and/or cationic and/or ampholytic and/or zwitterionic and/or semipolar surfactants.

The surfactant is typically present at a level of from 0.1% to 60% by weight. More preferred levels of incorporation are 1% to 35% by weight, most preferably from 1% to 20% by weight of machine laundry and rinse added fabric softener compositions in accord with the invention.

The surfactant is preferably formulated to be compatible with enzyme components present in the composition. In liquid or gel compositions the surfactant is most preferably formulated such that it promotes, or at least does not degrade, the stability of any enzyme in these compositions.

Preferred non-alkylbenzene sulfonate surfactant systems to be used according to the present invention comprise as a surfactant one or more of the nonionic and/or anionic surfactants described herein.

Polyethylene, polypropylene, and polybutylene oxide condensates of alkyl phenols are suitable for use as the nonionic surfactant of the surfactant systems of the present invention, with the polyethylene oxide condensates being preferred. These compounds include the condensation products of alkyl phenols having an alkyl group containing from about 6 to about 14 carbon atoms, preferably from about 8 to about 14 carbon atoms, in either a straight-chain or branched-chain configuration with the alkylene oxide. In a preferred embodiment, the ethylene oxide is present in an amount equal to from about 2 to about 25 moles, more preferably from about 3 to about 15 moles, of ethylene oxide per mole of alkyl phenol. Commercially available nonionic surfactants of this type include Igepal™ CO-630, marketed by the GAF Corporation; and Triton™ X-45, X-114, X-100 and X-102, all marketed by the Rohm & Haas Company. These surfactants are commonly referred to as alkylphenol alkoxylates (e.g., alkyl phenol ethoxylates).

The condensation products of primary and secondary aliphatic alcohols with from about 1 to about 25 moles of ethylene oxide are suitable for use as the nonionic surfactant of the nonionic surfactant systems of the present invention. The alkyl chain of the aliphatic alcohol can either be straight or branched, primary or secondary, and generally contains from about 8 to about 22 carbon atoms. Preferred are the condensation products of alcohols having an alkyl group containing from about 8 to about 20 carbon atoms, more preferably from about 10 to about 18 carbon atoms, with from about 2 to about 10 moles of ethylene oxide per mole of alcohol. About 2 to about 7 moles of ethylene oxide and most preferably from 2 to 5 moles of ethylene oxide per mole of alcohol are present in said condensation products. Examples of commercially available nonionic surfactants of this type include Tergitol™ 15-S-9 (the condensation product of $C_{11}$–$C_{15}$ linear alcohol with 9 moles ethylene oxide), Tergitol™ 24-L-6 NMW (the condensation product of $C_{12}$–$C_{14}$ primary alcohol with 6 moles ethylene oxide with a narrow molecular weight distribution), both marketed by Union Carbide Corporation; Neodol™ 45-9 (the condensation product of $C_{14}$–$C_{15}$ linear alcohol with 9 moles of ethylene oxide), Neodol™ 23-3 (the condensation product of $C_{12}$–$C_{13}$ linear alcohol with 3.0 moles of ethylene oxide), Neodol™ 45-7 (the condensation product of $C_{14}$–$C_{15}$ linear alcohol with 7 moles of ethylene oxide), Neodol™ 45-5 (the condensation product of $C_{14}$–$C_{15}$ linear alcohol with 5 moles of ethylene oxide) marketed by, Shell Chemical Company, Kyro™ EOB (the condensation product of $C_{13}$–$C_{15}$ alcohol with 9 moles ethylene oxide), marketed by The Procter & Gamble Company, and Genapol LA O5O (the condensation product of $C_{12}$–$C_{14}$ alcohol with 5 moles of ethylene oxide) marketed by Hoechst. Preferred range of HLB in these products is from 8–11 and most preferred from 8–10.

Also useful as the nonionic surfactant of the surfactant systems of the present invention are the alkylpolysaccharides disclosed in U.S. Pat. No. 4,565,647, Llenado, issued Jan. 21, 1986, having a hydrophobic group containing from about 6 to about 30 carbon atoms, preferably from about 10 to about 16 carbon atoms and a polysaccharide, e.g. a polyglycoside, hydrophilic group containing from about 1.3 to about 10, preferably from about 1.3 to about 3, most preferably from about 1.3 to about 2.7 saccharide units. Any reducing saccharide containing 5 or 6 carbon atoms can be used, e.g., glucose, galactose and galactosyl moieties can be substituted for the glucosyl moieties (optionally the hydrophobic group is attached at the 2-, 3-, 4-, etc. positions thus giving a glucose or galactose as opposed to a glucoside or galactoside). The intersaccharide bonds can be, e.g., between the one position of the additional saccharide units and the 2-, 3-, 4-, and/or 6- positions on the preceding saccharide units.

The preferred alkylpolyglycosides have the formula $$R^2O(C_nH_{2n}O)_t(glycosyl)_x$$

wherein $R^2$ is selected from the group consisting of alkyl, alkylphenyl, hydroxyalkyl, hydroxyalkylphenyl, and mixtures thereof in which the alkyl groups contain from about 10 to about 18, preferably from about 12 to about 14, carbon atoms; n is 2 or 3, preferably 2; t is from 0 to about 10, preferably 0; and x is from about 1.3 to about 10, preferably from about 1.3 to about 3, most preferably from about 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominately the 2-position.

The condensation products of ethylene oxide with a hydrophobic base formed by the condensation of propylene oxide with propylene glycol are also suitable for use as the additional nonionic surfactant systems of the present invention. The hydrophobic portion of these compounds will preferably have a molecular weight of from about 1500 to about 1800 and will exhibit water insolubility. The addition of polyoxyethylene moieties to this hydrophobic portion tends to increase the water solubility of the molecule as a whole, and the liquid character of the product is retained up to the point where the polyoxyethylene content is about 50% of the total weight of the condensation product, which corresponds to condensation with up to about 40 moles of ethylene oxide. Examples of compounds of this type include certain of the commercially-available Pluronic™ surfactants, marketed by BASF.

Also suitable for use as the nonionic surfactant of the nonionic surfactant system of the present invention, are the condensation products of ethylene oxide with the product resulting from the reaction of propylene oxide and ethylenediamine. The hydrophobic moiety of these products consists of the reaction product of ethylenediamine and excess propylene oxide, and generally has a molecular weight of from about 2500 to about 3000. This hydrophobic moiety is condensed with ethylene oxide to the extent that the condensation product contains from about 40% to about 80% by weight of polyoxyethylene and has a molecular weight of from about 5,000 to about 11,000. Examples of this type of nonionic surfactant include certain of the commercially available Tetronic™ compounds, marketed by BASF.

Preferred for use as the nonionic surfactant of the surfactant systems of the present invention are polyethylene oxide condensates of alkyl phenols, condensation products of primary and secondary aliphatic alcohols with from about 1 to about 25 moles of ethylene oxide, alkylpolysaccharides, and mixtures thereof. Most preferred are $C_8$–$C_{14}$ alkyl phenol ethoxylates having from 3 to 15 ethoxy groups and $C_8$–$C_{18}$ alcohol ethoxylates (preferably $C_{10}$ avg.) having from 2 to 10 ethoxy groups, and mixtures thereof.

Highly preferred nonionic surfactants are polyhydroxy fatty acid amide surfactants of the formula.

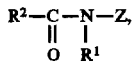

wherein $R^1$ is H, or $R^1$ is $C_{1-4}$ hydrocarbyl, 2-hydroxy ethyl, 2-hydroxy propyl or a mixture thereof, $R^2$ is $C_{5-31}$ hydrocarbyl, and Z is a polyhydroxyhydrocarbyl having a linear hydrocarbyl chain with at least 3 hydroxyls directly connected to the chain, or an alkoxylated derivative thereof. Preferably, $R^1$ is methyl, $R^2$ is a straight $C_{11-15}$ alkyl or $C_{16-18}$ alkyl or alkenyl chain such as coconut alkyl or mixtures thereof, and Z is derived from a reducing sugar such as glucose, fructose, maltose, lactose, in a reductive amination reaction.

When included in such laundry detergent compositions, the nonionic surfactant systems of the present invention act to improve the greasy/oily stain removal properties of such laundry detergent compositions across a broad range of laundry conditions.

Highly preferred anionic surfactants include alkyl alkoxylated sulfate surfactants hereof are water soluble salts or acids of the formula RO(A)$_m$SO3M wherein R is an unsubstituted $C_{10}$–$C_{24}$ alkyl or hydroxyalkyl group having a $C_{10}$–$C_{24}$ alkyl component, preferably a $C_{12}$–$C_{20}$ alkyl or hydroxyalkyl, more preferably $C_{12}$–$C_{18}$ alkyl or hydroxyalkyl, A is an ethoxy or propoxy unit, m is greater than zero, typically between about 0.5 and about 6, more preferably between about 0.5 and about 3, and M is H or a cation which can be, for example, a metal cation (e.g., sodium, potassium, lithium, calcium, magnesium, etc.), ammonium or substituted-ammonium cation. Alkyl ethoxylated sulfates as well as alkyl propoxylated sulfates are contemplated herein. Specific examples of substituted ammonium cations include methyl-, dimethyl, trimethylammonium cations and quaternary ammonium cations such as tetramethyl-ammonium and dimethyl piperdinium cations and those derived from alkylamines such as ethylamine, diethylamine, triethylamine, mixtures thereof, and the like. Exemplary surfactants are $C_{12}$–$C_{18}$ alkyl polyethoxylate (1.0) sulfate ($C_{12}$–$C_{18}$E(1.0)M), $C_{12}$–$C_{18}$ alkyl polyethoxylate (2.25) sulfate ($C_{12}$–$C_{18}$E(2.25)M), $C_{12}$–$C_{18}$ alkyl polyethoxylate (3.0) sulfate ($C_{12}$–$C_{18}$E(3.0)M), and $C_{12}$–$C_{18}$ alkyl polyethoxylate (4.0) sulfate ($C_{12}$–$C_{18}$ E(4.0)M), wherein M is conveniently selected from sodium and potassium.

Suitable anionic surfactants to be used are alkyl ester sulfonate surfactants including linear esters of $C_8$–$C_{20}$ carboxylic acids (i.e., fatty acids) which are sulfonated with gaseous $SO_3$ according to "The Journal of the American Oil Chemists Society", 52 (1975), pp. 323–329. Suitable starting materials would include natural fatty substances as derived from tallow, palm oil, etc.

The preferred alkyl ester sulfonate surfactant, especially for laundry applications, comprise alkyl ester sulfonate surfactants of the structural formula:

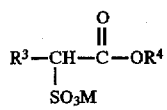

wherein $R^3$ is a $C_8$–$C_{20}$ hydrocarbyl, preferably an alkyl, or combination thereof, $R^4$ is a $C_1$–$C_6$ hydrocarbyl, preferably an alkyl, or combination thereof, and M is a cation which forms a water soluble salt with the alkyl ester sulfonate. Suitable salt-forming cations include metals such as sodium, potassium, and lithium, and substituted or unsubstituted ammonium cations, such as monoethanolamine, diethanolamine, and triethanolamine. Preferably, $R^3$ is $C_{10}$–$C_{16}$ alkyl, and $R^4$ is methyl, ethyl or isopropyl. Especially preferred are the methyl ester sulfonates wherein $R^3$ is $C_{10}$–$C_{16}$ alkyl.

Other suitable anionic surfactants include the alkyl sulfate surfactants which are water soluble salts or acids of the formula ROSO3M wherein R preferably is a $C_{10}$–$C_{24}$ hydrocarbyl, preferably an alkyl or hydroxyalkyl having a $C_{10}$–$C_{20}$ alkyl component, more preferably a $C_{12}$–$C_{18}$ alkyl or hydroxyalkyl, and M is H or a cation, e.g., an alkali metal cation (e.g. sodium, potassium, lithium), or ammonium or substituted ammonium (e.g. methyl-, dimethyl-, and trimethyl ammonium cations and quaternary ammonium cations such as tetramethyl-ammonium and dimethyl piperdinium cations and quaternary ammonium cations derived from alkylamines such as ethylamine, diethylamine, triethylamine, and mixtures thereof, and the like). Typically, alkyl chains of $C_{12}$–$C_{16}$ are preferred for lower wash temperatures (e.g. below about 50° C.) and $C_{16-18}$ alkyl chains are preferred for higher wash temperatures (e.g. above about 50° C.).

Other anionic surfactants useful for detersive purposes can also be included in the laundry detergent compositions of the present invention. These can include salts (including, for example, sodium, potassium, ammonium, and substituted ammonium salts such as mono-, di- and triethanolamine salts) of soap, $C_8$–$C_{22}$ primary of secondary alkanesulfonates, $C_8$–$C_{24}$ olefinsulfonates, sulfonated polycarboxylic acids prepared by sulfonation of the pyrolyzed product of alkaline earth metal citrates, e.g., as described in British patent specification No. 1,082,179, $C_8$–$C_{24}$ alkylpolyglycolethersulfates (containing up to 10 moles of ethylene oxide); alkyl glycerol sulfonates, fatty acyl glycerol sulfonates, fatty oleyl glycerol sulfates, alkyl phenol ethylene oxide ether sulfates, paraffin sulfonates, alkyl phosphates, isethionates such as the acyl isethionates, N-acyl taurates, alkyl succinamates and sulfosuccinates, monoesters of sulfosuccinates (especially saturated and unsaturated $C_{12}$–$C_{18}$ monoesters) and diesters of sulfosuccinates (especially saturated and unsaturated $C_6$–$C_{12}$ diesters), acyl sarcosinates, sulfates of alkylpolysaccharides such as the sulfates of alkylpolyglucoside (the nonionic nonsulfated compounds being described below), branched primary alkyl sulfates, and alkyl polyethoxy carboxylates such as those of the formula $RO(CH_2CH_2O)_k$—$CH_2COO$—M+ wherein R is a $C_8$–$C_{22}$ alkyl, k is an integer from 1 to 10, and M is a soluble salt-forming cation. Resin acids and hydrogenated resin acids are also suitable, such as rosin, hydrogenerated rosin, and resin acids and hydrogenated resin acids present in or derived from tall oil.

Further examples are described in "Surface Active Agents and Detergents" (Vol. I and II by Schwartz, Perry and Berch). A variety of such surfactants are also generally disclosed in U.S. Pat. No. 3,929,678, issued Dec. 30, 1975 to Laughlin, et al. at Column 23, line 58 through Column 29, line 23 (herein incorporated by reference). When included therein, the laundry detergent compositions of the present invention typically comprise from about 1% to about 40%, preferably from about 3% to about 20% by weight of such anionic surfactants.

The laundry detergent compositions of the present invention may also contain cationic, ampholytic, zwitterionic, and semi-polar surfactants, as well as the nonionic and/or anionic surfactants other than those already described herein. Cationic detersive surfactants suitable for use in the laundry detergent compositions of the present invention are those having one long-chain hydrocarbyl group. Examples of such cationic surfactants include the ammonium surfactants such as alkyltrimethylammonium halogenides, and those surfactants having the formula:

$$[R^2(OR^3)_y][R^4(OR^3)_y]_2R^5N+X—$$

wherein $R^2$ is an alkyl or alkyl benzyl group having from about 8 to about 18 carbon atoms in the alkyl chain, each $R^3$ is selected from the group consisting of —$CH_2CH_2$—, —$CH_2CH(CH_3)$—, —$CH_2CH(CH_2OH)$—, —$CH_2CH_2CH_2$—, and mixtures thereof; each $R^4$ is selected from the group consisting of $C_1$–$C_4$ alkyl, $C_1$–$C_4$ hydroxyalkyl, benzyl ring structures formed by joining the two $R^4$ groups, —$CH_2CHOH$—$CHOHCOR^6CHOHCH_2OH$ wherein $R^6$ is any hexose or hexose polymer having a molecular weight less than about 1000, and hydrogen when y is not 0; $R^5$ is the same as $R^4$ or is an alkyl chain wherein the total number of carbon atoms of $R^2$ plus $R^5$ is not more than about 18; each y is from 0 to about 10 and the sum of the y values is from 0 to about 15; and X is any compatible anion.

Highly preferred cationic surfactants are the water-soluble quaternary ammonium compounds useful in the present composition having the formula:

$$R_1R_2R_3R_4N^+X^- (i)$$

wherein $R_1$ is $C_8$–$C_{16}$ alkyl, each of $R_2$, $R_3$ and $R_4$ is independently $C_1$–$C_4$ alkyl, $C_1$–$C_4$ hydroxy alkyl, benzyl, and —$(C_2H_4O)_xH$ where x has a value from 2 to 5, and X is an anion. Not more than one of $R_2$, $R_3$ or $R_4$ should be benzyl. The preferred alkyl chain length for $R_1$ is $C_{12}$–$C_{15}$ particularly where the alkyl group is a mixture of chain lengths derived from coconut or palm kernel fat or is derived synthetically by olefin build up or OXO alcohols synthesis. Preferred groups for $R_2R_3$ and $R_4$ are methyl and hydroxyethyl groups and the anion X may be selected from halide, methosulphate, acetate and phosphate ions.

Examples of suitable quaternary ammonium compounds of formulae (i) for use herein are:

coconut trimethyl ammonium chloride or bromide;
coconut methyl dihydroxyethyl ammonium chloride or bromide;
decyl triethyl ammonium chloride;
decyl dimethyl hydroxyethyl ammonium chloride or bromide;
$C_{12-15}$ dimethyl hydroxyethyl ammonium chloride or bromide;
coconut dimethyl hydroxyethyl ammonium chloride or bromide;
myristyl trimethyl ammonium methyl sulphate;
lauryl dimethyl benzyl ammonium chloride or bromide;
lauryl dimethyl (ethenoxy)$_4$ ammonium chloride or bromide;
choline esters (compounds of formula (i) wherein $R_1$ is $CH_2$—$CH_2$—O—C(O)—$C_{12-14}$ alkyl and $R_2R_3R_4$ are methyl);
di-alkyl imidazolines [compounds of formula (i)].

Other cationic surfactants useful herein are also described in U.S. Pat. No. 4,228,044, Cambre, issued Oct. 14, 1980 and in European Patent Application EP 000,224.

When included therein, the laundry detergent compositions of the present invention typically comprise from 0.2% to about 25%, preferably from about 1% to about 8% by weight of such cationic surfactants.

Ampholytic surfactants are also suitable for use in the laundry detergent compositions of the present invention. These surfactants can be broadly described as aliphatic derivatives of secondary or tertiary amines, or aliphatic derivatives of heterocyclic secondary and tertiary amines in which the aliphatic radical can be straight- or branched-chain. One of the aliphatic substituents contains at least about 8 carbon atoms, typically from about 8 to about 18 carbon atoms, and at least one contains an anionic water-solubilizing group, e.g. carboxy, sulfonate, sulfate. See U.S. Pat. No. 3,929,678 to Laughlin et al., issued Dec. 30, 1975 at column 19, lines 18–35, for examples of ampholytic surfactants.

When included therein, the laundry detergent compositions of the present invention typically comprise from 0.2% to about 15%, preferably from about 1% to about 10% by weight of such ampholytic surfactants.

Zwitterionic surfactants are also suitable for use in laundry detergent compositions. These surfactants can be broadly described as derivatives of secondary and tertiary amines, derivatives of heterocyclic secondary and tertiary amines, or derivatives of quaternary ammonium, quaternary phosphonium or tertiary sulfonium compounds. See U.S. Pat. No. 3,929,678 to Laughlin et al., issued Dec. 30, 1975 at column 19, line 38 through column 22, line 48, for examples of zwitterionic surfactants.

When included therein, the laundry detergent compositions of the present invention typically comprise from 0.2% to about 15%, preferably from about 1% to about 10% by weight of such zwitterionic surfactants.

Semi-polar nonionic surfactants are a special category of nonionic surfactants which include water-soluble amine oxides containing one alkyl moiety of from about 10 to about 18 carbon atoms and 2 moieties selected from the group consisting of alkyl groups and hydroxyalkyl groups containing from about 1 to about 3 carbon atoms; water-soluble phosphine oxides containing one alkyl moiety of from about 10 to about 18 carbon atoms and 2 moieties selected from the group consisting of alkyl groups and hydroxyalkyl groups containing from about 1 to about 3 carbon atoms; and water-soluble sulfoxides containing one alkyl moiety of from about 10 to about 18 carbon atoms and a moiety selected from the group consisting of alkyl and hydroxyalkyl moieties of from about 1 to about 3 carbon atoms.

Semi-polar nonionic detergent surfactants include the amine oxide surfactants having the formula

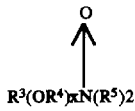

$$R^3(OR^4)_xN(R^5)_2$$

wherein $R^3$ is an alkyl, hydroxyalkyl, or alkyl phenyl group or mixtures thereof containing from about 8 to about 22 carbon atoms; $R^4$ is an alkylene or hydroxyalkylene group containing from about 2 to about 3 carbon atoms or mixtures thereof; x is from 0 to about 3; and each $R^5$ is an alkyl or hydroxyalkyl group containing from about 1 to about 3 carbon atoms or a polyethylene oxide group containing from about 1 to about 3 ethylene oxide groups. The $R^5$ groups can be attached to each other, e.g., through an oxygen or nitrogen atom, to form a ring structure.

These amine oxide surfactants in particular include $C_{10}$–$C_{18}$ alkyl dimethyl amine oxides and $C_8$–$C_{12}$ alkoxy ethyl dihydroxy ethyl amine oxides.

When included therein, the laundry detergent compositions of the present invention typically comprise from 0.2% to about 15%, preferably from about 1% to about 10% by weight of such semi-polar nonionic surfactants.

Detergent Components

The detergent compositions of the invention may also contain additional detergent components. The precise nature of these additional components, and levels of incorporation thereof will depend on the physical form of the composition, and the nature of the cleaning operation for which it is to be used.

The compositions of the invention may for example, be formulated as hand and machine laundry detergent compositions including laundry additive compositions and compositions suitable for use in the pretreatment of stained fabrics, and rinse added fabric softener compositions.

When formulated as compositions suitable for use in a machine washing method, the compositions of the invention preferably contain both a surfactant and a builder compound and additionally one or more detergent components preferably selected from organic polymeric compounds, bleaching agents, additional enzymes, suds suppressors, dispersants, lime-soap dispersants, soil suspension and anti-redeposition agents and corrosion inhibitors. Laundry compositions can also contain softening agents, as additional detergent components.

If needed the density of the laundry detergent compositions herein ranges from 550 to 1000 g/liter, preferably 600 to 950 g/liter of composition measured at 20° C.

The "compact" form of the compositions herein is best reflected by density and, in terms of composition, by the amount of inorganic filler salt; inorganic filler salts are conventional ingredients of detergent compositions in powder form; in conventional detergent compositions, the filler salts are present in substantial mounts, typically 17–35% by weight of the total composition.

In the compact compositions, the filler salt is present in mounts not exceeding 15% of the total composition, preferably not exceeding 10%, most preferably not exceeding 5% by weight of the composition.

The inorganic filler salts, such as meant in the present compositions are selected from the alkali and alkaline-earth-metal salts of sulphates and chlorides. A preferred filler salt is sodium sulphate.

Optional Detergent Ingredients:

Preferred detergent compositions of the present invention may further comprise an enzyme which provides cleaning performance and/or fabric care benefits. Said enzymes include enzymes selected from cellulases, hemicellulases, peroxidases, gluco-amylases, amylases, cutinases, pectinases, xylanases, reductases, oxidases, phenoloxidases, lipoxygenases, ligninases, pullulanases, tannases, pentosanases, malanases, β-glucanases, arabinosidases or mixtures thereof.

A preferred combination is a detergent composition having a cocktail of conventional applicable enzymes like amylase, cutinase and/or cellulase in conjunction with the lipolytic and protealytic enzymes.

The cellulases usable in the present invention include both bacterial or fungal cellulase. Preferably, they will have a pH optimum of between 5 and 9.5. Suitable cellulases are disclosed in U.S. Pat. No. 4,435,307, Barbesgoard et al, which discloses fungal cellulase produced from *Humicola insolens*. Suitable cellulases are also disclosed in GB-A-2.075.028; GB-A-2.095.275 and DE-OS-2.247.832.

Examples of such cellulases are cellulases produced by a strain of *Humicola insolens* (*Humicola grisea* var. *thermoidea*), particularly the Humicola strain DSM 1800.

Other suitable cellulases are cellulases originated from *Humicola insolens* having a molecular weight of about 50 KDa, an isoelectric point of 5.5 and containing 415 amino acids. Especially suitable cellulases are the cellulases having color care benefits. Examples of such cellulases are cellulases described in European patent application No. 91202879.2, filed Nov. 6, 1991 (Novo).

Peroxidase enzymes are used in combination with oxygen sources, e.g. percarbonate, perborate, persulfate, hydrogen peroxide, etc. They are used for "solution bleaching", i.e. to prevent transfer of dyes or pigments removed from substrates during wash operations to other substrates in the wash solution.

Peroxidase enzymes are known in the art, and include, for example, horseradish peroxidase, ligninase, and haloperoxidase such as chloro- and bromo-peroxidase. Peroxidase-containing detergent compositions are disclosed, for example, in PCT International Application WO 89/099813 and in European Patent application EP No. 91202882.6, filed on Nov. 6, 1991.

Said cellulases and/or peroxidases are normally incorporated in the detergent composition at levels from 0.0001% to 2% of active enzyme by weight of the detergent composition.

Also suitable are cutinases [EC 3.1.1.50] which can be considered as a special kind of lipase, namely lipases which do not require interfacial activation. Addition of cutinases to detergent compositions have been described in e.g. WO-A-88/09367 (Genencor). The cutinases are normally incorporated in the detergent composition at levels from 0.0001% to 2% of active enzyme by weight of the detergent composition.

Amylases (α and/or β) can be included for removal of carbohydrate-based stains. Suitable amylases are Termamyl$^R$ (Novo Nordisk), Fungamyl$^R$ and BAN$^R$ (Novo Nordisk). The above-mentioned enzymes may be of any suitable origin, such as vegetable, animal, bacterial, fungal and yeast origin.

Said enzymes are normally incorporated in the detergent composition at levels from 0.0001% to 2% of active enzyme by weight of the detergent composition. Other suitable detergent ingredients that can be added are enzyme oxidation scavengers which are described in Copending European Patent application 92870018.6 filed on Jan. 31, 1992. Examples of such enzyme oxidation scavengers are ethoxylated tetraethylene polyamines.

Especially preferred detergent ingredients are combinations with technologies which also provide a type of color care benefit. Examples of these technologies are metallo catalysts for color maintenance. Such metallo catalysts are described in copending European Patent Application No. 92870181.2.

Additional optional detergent ingredients that can be included in the detergent compositions of the present invention include bleaching agents such as PB 1, PB4 and percarbonate with a particle size of 400–800 microns. These bleaching agent components can include one or more oxygen bleaching agents and, depending upon the bleaching agent chosen, one or more bleach activators. When present oxygen bleaching compounds will typically be present at levels of from about 1% to about 25%. In general, bleaching compounds are optional components in non-liquid formulations, e.g. granular detergents.

The bleaching agent component for use herein can be any of the bleaching agents useful for detergent compositions including oxygen bleaches as well as others known in the art.

The bleaching agent suitable for the present invention can be an activated or non-activated bleaching agent.

One category of oxygen bleaching agent that can be used encompasses percarboxylic acid bleaching agents and salts thereof. Suitable examples of this class of agents include magnesium monoperoxyphthalate hexahydrate, the magnesium salt of meta-chloro perbenzoic acid, 4-nonylamino-4-oxoperoxybutyric acid and diperoxydodecanedioic acid. Such bleaching agents are disclosed in U.S. Pat. No. 4,483,781, U.S. patent application Ser. No. 740,446, European Patent Application 0,133,354 and U.S. Pat. No. 4,412,934. Highly preferred bleaching agents also include 6-nonylamino-6-oxoperoxycaproic acid as described in U.S. Pat. No. 4,634,551.

Another category of bleaching agents that can be used encompasses the halogen bleaching agents. Examples of hypohalite bleaching agents, for example, include trichloro isocyanuric acid and the sodium and potassium dichloroisocyanurates and N-chloro and N-bromo alkane sulphonamides. Such materials are normally added at 0.5–10% by weight of the finished product, preferably 1–5% by weight.

The hydrogen peroxide releasing agents can be used in combination with bleach activators such as tetraacetylethylenediamine (TAED), nonanoyloxybenzene-sulfonate (NOBS, described in U.S. Pat. No. 4,412,934), 3,5,-trimethylhexanoloxybenzenesulfonate (ISONOBS, described in EP 120,591) or pentaacetylglucose (PAG), which are perhydrolyzed to form a peracid as the active bleaching species, leading to improved bleaching effect. Also suitable activators are acylated citrate esters such as disclosed in Copending European Patent Application No. 91870207.7.

Useful bleaching agents, including peroxyacids and bleaching systems comprising bleach activators and peroxygen bleaching compounds for use in cleaning compositions according to the invention are described in our co-pending application U.S. Ser. No. 08/136,626.

The hydrogen peroxide may also be present by adding an enzymatic system (i.e. an enzyme and a substrate therefore) which is capable of generating hydrogen peroxide at the beginning or during the washing and/or rinsing process. Such enzymatic systems are disclosed in EP Patent Application 91202655.6 filed Oct. 9, 1991.

Bleaching agents other than oxygen bleaching agents are also known in the art and can be utilized herein. One type of non-oxygen bleaching agent of particular interest includes photoactivated bleaching agents such as the sulfonated zinc and/or aluminum phthalocyanines. These materials can be deposited upon the substrate during the washing process. Upon irradiation with light, in the presence of oxygen, such as by hanging clothes out to dry in the daylight, the sulfonated zinc phthalocyanine is activated and, consequently, the substrate is bleached. Preferred zinc phthalocyanine and a photoactivated bleaching process are described in U.S. Pat. No. 4,033,718. Typically, detergent compositions will contain about 0.025% to about 1.25%, by weight, of sulfonated zinc phthalocyanine.

The compositions according to the present invention may further comprise a builder system. Any conventional builder system is suitable for use herein including aluminosilicate materials, silicates, polycarboxylates and fatty acids, materials such as ethylenediamine tetraacetate, metal ion sequestrants such as aminopolyphosphonates, particularly ethylenediamine tetramethylene phosphortic acid and diethylene triamine pentamethylenephosphonic acid. Though less preferred for obvious environmental reasons, phosphate builders can also be used herein.

Suitable builders can be an inorganic ion exchange material, commonly an inorganic hydrated aluminosilicate material, more particularly a hydrated synthetic zeolite such as hydrated zeolite A, X, B, HS or MAP.

Another suitable inorganic builder material is layered silicate, e.g. SKS-6 (Hoechst). SKS-6 is a crystalline layered silicate consisting of sodium silicate ($Na_2Si_2O_5$).

Suitable polycarboxylates containing one carboxy group include lactic acid, glycolic acid and ether derivatives thereof as disclosed in Belgian Patent Nos. 831,368, 821,369 and 821,370. Polycarboxylates containing two carboxy groups include the water-soluble salts of succinic acid, malonic acid, (ethylenedioxy) diacetic acid, maleic acid, diglycollic acid, tartaric acid, tartronic acid and fumaric acid, as well as the ether carboxylates described in German Offenlegenschrift 2,446,686, and 2,446,687 and U.S. Pat. No. 3,935,257 and the sulfinyl carboxylates described in Belgian Patent No. 840,623. Polycarboxylates containing three carboxy groups include, in particular, water-soluble citrates, aconitrates and citraconates as well as succinate derivatives such as the carboxymethyloxysuccinates described in British Patent No. 1,379,241, lactoxysuccinates described in Netherlands Application 7205873, and the oxypolycarboxylate materials such as 2-oxa-1,1,3-propane tricarboxylates described in British Patent No. 1,387,447.

Polycarboxylates containing four carboxy groups include oxydisuccinates disclosed in British Patent No. 1,261,829, 1,1,2,2-ethane tetracarboxylates, 1, 1,3,3-propane tetracarboxylates and 1,1,2,3-propane tetracarboxylates. Polycarboxylates containing sulfo substituents include the sulfosuccinate derivatives disclosed in British Patent Nos. 1,398,421 and 1,398,422 and in U.S. Pat. No. 3,936,448, and the sulfonated pyrolysed titrates described in British Patent No. 1,082,179, while polycarboxylates containing phosphone substituents are disclosed in British Patent No. 1,439,000.

Alicyclic and heterocyclic polycarboxylates include cyclopentane-cis,cis, cis-tetracarboxylates, cyclopentadienide pentacarboxylates, 2,3,4,5-tetrahydro-furan -cis, cis, cis-tetracarboxylates, 2,5-tetrahydro-furan -cis-dicarboxylates, 2,2,5,5-tetrahydrofuran-tetracarboxylates, 1,2,3,4,5,6-hexane -hexacar-boxylates and and carboxymethyl derivatives of polyhydric alcohols such as sorbitol, mannitol and xylitol. Aromatic poly-carboxylates include mellitic acid, pyromellitic acid and the phthalic acid derivatives disclosed in British Patent No. 1,425,343.

Of the above, the preferred polycarboxylates are hydroxycarboxylates containing up to three carboxy groups per molecule, more particularly citrates.

Preferred builder systems for use in the present compositions include a mixture of a water-insoluble aluminosilicate builder such as zeolite A or of a layered silicate (SKS-6), and a water-soluble carboxylate chelating agent such as citric acid.

A suitable chelant for inclusion in the detergent compositions in accordance with the invention is ethylenediamine-N,N'-disuccinic acid (EDDS) or the alkali metal, alkaline earth metal, ammonium, or substituted ammonium salts thereof, or mixtures thereof. Preferred EDDS compounds are the free acid form and the sodium or magnesium salt thereof. Examples of such preferred sodium salts of EDDS include $Na_2$EDDS and $Na_4$EDDS. Examples of such preferred magnesium salts of EDDS include MgEDDS and $Mg_2$EDDS. The magnesium salts are the most preferred for inclusion in compositions in accordance with the invention.

Preferred builder systems include a mixture of a water-insoluble aluminosilicate builder such as zeolite A, and a watersoluble carboxylate chelating agent such as citric acid. Other builder materials that can form part of the builder system for use in granular compositions include inorganic materials such as alkali metal carbonates, bicarbonates, silicates, and organic materials such as the organic phosphonates, amino polyalkylene phosphonates and amino polycarboxylates.

Other suitable water-soluble organic salts are the homo- or co-polymeric acids or their salts, in which the polycarboxylic acid comprises at least two carboxyl radicals separated from each other by not more than two carbon atoms. Polymers of this type are disclosed in GB-A-1,596,756. Examples of such salts are polyacrylates of MW 2000–5000 and their copolymers with maleic anhydride, such copolymers having a molecular weight of from 20,000 to 70,000, especially about 40,000.

Detergency builder salts are normally included in amounts of from 10% to 80% by weight of the composition preferably from 20% to 70% and most usually from 30% to 60% by weight.

Another optional ingredient is a suds suppressor, exemplified by silicones, and silica-silicone mixtures. Silicones can be generally represented by alkylated polysiloxane materials while silica is normally used in finely divided forms exemplified by silica aerogels and xerogels and hydrophobic silicas of various types. These materials can be incorporated as particulates in which the suds suppressor is advantageously releasably incorporated in a water-soluble or water-dispersible, substantially non-surface-active detergent impermeable carrier. Alternatively the suds suppressor can be dissolved or dispersed in a liquid carrier and applied by spraying on to one or more of the other components.

A preferred silicone suds controlling agent is disclosed in Bartollota et al. U.S. Pat. No. 3,933,672. Other particularly useful suds suppressors are the self-emulsifying silicone suds suppressors, described in German Patent Application DTOS 2 646 126 published Apr. 28, 1977. An example of such a compound is DC-544, commercially available from Dow Corning, which is a siloxane-glycol copolymer. Especially preferred suds controlling agent are the suds suppressor system comprising a mixture of silicone oils and 2-alkyl-alcanols. Suitable 2-alkyl-alkanols are 2-butyl-octanol which are commercially available under the trade name Isofol 12 R.

Such suds suppressor system are described in Copending European Patent application N 92870174.7 filed 10 Nov., 1992.

Especially preferred silicone suds controlling agents are described in Copending European Patent application No. 92201649.8. Said compositions can comprise a silicone/silica mixture in combination with fumed nonporous silica such as Aerosil$^R$.

The suds suppressors described above are normally employed at levels of from 0.001% to 2% by weight of the composition, preferably from 0.01% to 1% by weight.

Other components used in detergent compositions may be employed, such as soil-suspending agents, soil-release agents, optical brighteners, abrasives, bactericides, tarnish inhibitors, coloring agents, and/or encapsulated or non-encapsulated perfumes.

Especially suitable encapsulating materials are water soluble capsules which consist of a matrix of polysaccharide and polyhydroxy compounds such as described in GB 1,464,616.

Other suitable water soluble encapsulating materials comprise dextrins derived from ungelatinized starch acid-esters of substituted dicarboxylic acids such as described in U.S. Pat. No. 3,455,838. These acid-ester dextrins are, preferably, prepared from such starches as waxy maize, waxy sorghum, sago, tapioca and potato. Suitable examples of said encapsulating materials include N-Lok manufactured by National Starch. The N-Lok encapsulating material consists of a modified maize starch and glucose. The starch is modified by adding monofunctional substituted groups such as octenyl succinic acid anhydride.

Antiredeposition and soil suspension agents suitable herein include cellulose derivatives such as methylcellulose, carboxymethylcellulose and hydroxyethylcellulose, and homo- or co-polymeric polycarboxylic acids or their salts. Polymers of this type include the polyacrylates and maleic anhydride-acrylic acid copolymers previously mentioned as builders, as well as copolymers of maleic anhydride with ethylene, methylvinyl ether or methacrylic acid, the maleic anhydride constituting at least 20 mole percent of the copolymer. These materials are normally used at levels of from 0.5% to 10% by weight, more preferably from 0.75% to 8%, most preferably from 1% to 6% by weight of the composition.

Preferred optical brighteners are anionic in character, examples of which are disodium 4,4'-bis-(2-diethanolamino-4-anilino-s-triazin-6-ylamino)stilbene-2:2'disulphonate, disodium 4,4'- bis-(2-morpholino-4-anilino-s-triazin-6-ylamino-stilbene-2:2'-disulphonate, disodium 4,4'-bis-(2,4-dianilino-s-triazin-6-ylamino)stilbene-2:2'-disulphonate, monosodium 4',4"-bis-(2,4-dianilino-s-tri-azin-6 ylamino) stilbene-2-sulphonate, disodium 4,4'-bis-(2-anilino-4-(N-methyl-N-2-hydroxyethylamino)-s-triazin-6-ylamino) stilbene-2,2'-disulphonate, di-sodium 4,4'-bis-(4-phenyl-2, 1,3-triazol-2-yl)-stilbene-2,2'disulphonate, di-so-dium 4,4'bis(2-anilino-4-(1-methyl-2-hydroxyethylamino)-s-triazin-6- ylami-no)stilbene-2,2'disulphonate, sodium 2(stilbyl-4"-(naphtho-,1',2':4,5)1,2,3 - triazole-2"-sulphonate and 4,4'-bis(2-sulphostyryl)biphenyl.

Other useful polymeric materials are the polyethylene glycols, particularly those of molecular weight 1000–10000, more particularly 2000 to 8000 and most preferably about 4000. These are used at levels of from 0.20% to 5% more preferably from 0.25% to 2.5% by weight. These polymers and the previously mentioned homo- or co-polymeric polycarboxylate salts are valuable for improving whiteness maintenance, fabric ash deposition, and cleaning performance on clay, proteinaceous and oxidizable soils in the presence of transition metal impurities.

Soil release agents useful in compositions of the present invention are conventionally copolymers or terpolymers of terephthalic acid with ethylene glycol and/or propylene glycol units in various arrangements. Examples of such polymers are disclosed in the commonly assigned U.S. Pat. Nos. 4,116,885 and 4,711,730 and European Published Patent Application No. 0 272 033. A particular preferred polymer in accordance with EP-A-0 272 033 has the formula

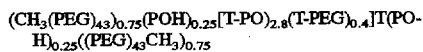

where PEG is $—(OC_2H_4)O—$, PO is $(OC_3H_6O)$ and T is $(pcOC_6H_4CO)$.

Also very useful are modified polyesters as random copolymers of dimethyl terephthalate, dimethyl sulfoisophthalate, ethylene glycol and 1–2 propane diol, the end groups consisting primarily of sulphobenzoate and secondarily of mono esters of ethylene glycol and/or propane-diol. The target is to obtain a polymer capped at both end by sulphobenzoate groups, "primarily", in the present context most of said copolymers herein will be end-capped by sulphobenzoate groups. However, some copolymers will be less than fully capped, and therefore their end groups may consist of monoester of ethylene glycol and/or propane 1–2 diol, thereof consist "secondarily" of such species.

The selected polyesters herein contain about 46% by weight of dimethyl terephthalic acid, about 16% by weight of propane –1.2 diol, about 10% by weight ethylene glycol about 13% by weight of dimethyl sulfobenzoic acid and about 15% by weight of sulfoisophthalic acid, and have a molecular weight of about 3.000. The polyesters and their method of preparation are described in detail in EPA 311 342.

Fabric softening agents can also be incorporated into laundry detergent compositions in accordance with the present invention. These agents may be inorganic or organic in type. Inorganic softening agents are exemplified by the smectite clays disclosed in GB-A-1 400 898 and in U.S. Pat. No. 5,019,292. Organic fabric softening agents include the water insoluble tertiary amines as disclosed in GB-A1 514 276 and EP-B0 011 340 and their combination with mono C12–C14 quaternary ammonium salts are disclosed in EP-B-0 026 527 and EP-B-0 026 528 and di-long-chain amides as disclosed in EP-B-0 242 919. Other useful organic ingredients of fabric softening systems include high molecular weight polyethylene oxide materials as disclosed in EP-A-0 299 575 and 0 313 146.

Levels of smectite clay are normally in the range from 5% to 15%, more preferably from 8% to 12% by weight, with the material being added as a dry mixed component to the remainder of the formulation. Organic fabric softening agents such as the water-insoluble tertiary amines or dilong chain amide materials are incorporated at levels of from 0.5% to 5% by weight, normally from 1% to 3% by weight whilst the high molecular weight polyethylene oxide materials and the water soluble cationic materials are added at levels of from 0.1% to 2%, normally from 0.15% to 1.5% by weight. These materials are normally added to the spray dried portion of the composition, although in some instances it may be more convenient to add them as a dry mixed particulate, or spray them as molten liquid on to other solid components of the composition.

The present invention also relates to a process for inhibiting dye transfer from one fabric to another of solubilized and suspended dyes encountered during fabric laundering operations involving colored fabrics.

The detergent compositions according to the present invention may comprise from 0.001% to 10 %, preferably from 0.01% to 2%, more preferably from 0.05% to 1% by weight of polymeric dye transfer inhibiting agents. Said polymeric dye transfer inhibiting agents are normally incorporated into detergent compositions in order to inhibit the transfer of dyes from colored fabrics onto fabrics washed therewith. These polymers have the ability to complex or adsorb the fugitive dyes washed out of dyed fabrics before the dyes have the opportunity to become attached to other articles in the wash.

Especially suitable polymeric dye transfer inhibiting agents are polyamine N-oxide polymers, copolymers of N-vinylpyrrolidone and N-vinylimidazole, polyvinylpyrrolidone polymers, polyvinyloxazolidones and polyvinylimidazoles or mixtures thereof.

The polyamine N-oxide polymers suitable for use contain units having the following structure formula:

wherein P is a polymerisable unit, whereto the R—N—O group can be attached to or wherein the R—N—O group forms part of the polymerisable unit or a combination of both.

A is $NC(O)$, $CO_2$, $C(O)$, —O—, —S—, —N—; x is 0 or 1;

R are aliphatic, ethoxylated aliphatics, aromatic, heterocyclic or alicyclic groups or any combination thereof whereto the nitrogen of the N—O group can be attached or wherein the nitrogen of the N—O group is part of these groups.

The N—O group can be represented by the following general structures:

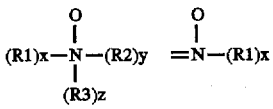

wherein R1, R2, and R3 are aliphatic groups, aromatic, heterocyclic or alicyclic groups or combinations thereof; x or/and y or/and z is 0 or 1 and wherein the nitrogen of the N—O group can be attached or wherein the nitrogen of the N—O group forms part of these groups.

The N—O group can be part of the polymerisable unit (P) or can be attached to the polymeric backbone or a combination of both. Suitable polyamine N-oxides wherein the N—O group forms pan of the polymerisable unit comprise polyamine N-oxides wherein R is selected from aliphatic, aromatic, alicyclic or heterocyclic groups.

One class of said polyamine N-oxides comprises the group of polyamine N-oxides wherein the nitrogen of the N—O group forms part of the R-group. Preferred polyamine N-oxides are those wherein R is a heterocyclic group such as pyrridine, pyrrole, imidazole, pyrrolidine, piperidine, quinoline, acridine and derivatives thereof.

Another class of said polyamine N-oxides comprises the group of polyamine N-oxides wherein the nitrogen of the N—O group is attached to the R-group.

Other suitable polyamine N-oxides are the polyamine oxides whereto the N—O group is attached to the polymerisable unit.

Preferred class of these polyamine N-oxides are the polyamine N-oxides having the general formula (I) wherein R is an aromatic, heterocyclic or alicyclic groups wherein the nitrogen of the N—O functional group is part of said R group.

Examples of these classes are polyamine oxides wherein R is a heterocyclic compound such as pyrridine, pyrrole, imidazole and derivatives thereof.

Another preferred class of polyamine N-oxides are the polyamine oxides having the general formula (I) wherein R are aromatic, heterocyclic or alicyclic groups wherein the nitrogen of the N—O functional group is attached to said R groups.

Examples of these classes are polyamine oxides wherein R groups can be aromatic such as phenyl.

Any polymer backbone can be used as long as the amine oxide polymer formed is water-soluble and has dye transfer inhibiting properties. Examples of suitable polymeric backbones are polyvinyls, polyalkylenes, polyesters, polyethers, polyamide, polyimides, polyacrylates and mixtures thereof.

The amine N-oxide polymers of the present invention typically have a ratio of amine to the amine N-oxide of 10:1 to 1:1000000. However the amount of amine oxide groups present in the polyamine oxide polymer can be varied by appropriate copolymerization or by appropriate degree of N-oxidation. Preferably, the ratio of amine to amine N-oxide is from 2:3 to 1:1000000. More preferably from 1:4 to 1:1000000, most preferably from 1:7 to 1:1000000. The polymers of the present invention actually encompass random or block copolymers where one monomer type is an amine N-oxide and the other monomer type is either an amine N-oxide or not. The amine oxide unit of the polyamine N-oxides has a $PKa<10$, preferably $PKa<7$, more preferred $PKa<6$.

The polyamine oxides can be obtained in almost any degree of polymerisation. The degree of polymerisation is not critical provided the material has the desired water-solubility and dye-suspending power.

Typically, the average molecular weight is within the range of 500 to 1000,000; preferably from 1,000 to 50,000, more preferably from 2,000 to 30,000, most preferably from 3,000 to 20,000.

The N-vinylimidazole N-vinylpyrrolidone polymers which may be used in the present invention have an average molecular weight range from 5,000–1,000,000, preferably from 20,000–200,000.

Highly preferred polymers for use in detergent compositions according to the present invention comprise a polymer selected from N-vinylimidazole N-vinylpyrrolidone copolymers wherein said polymer has an average molecular weight range from 5,000 to 50,000 more preferably from 8,000 to 30,000, most preferably from 10,000 to 20,000.

The average molecular weight range was determined by light scattering as described in Barth H. G. and Mays J. W. Chemical Analysis Vol 113,"Modern Methods of Polymer Characterization".

Highly preferred N-vinylimidazole N-vinylpyrrolidone copolymers have an average molecular weight range from 5,000 to 50,000; more preferably from 8,000 to 30,000; most preferably from 10,000 to 20,000.

The N-vinylimidazole N-vinylpyrrolidone copolymers characterized by having said average molecular weight range provide excellent dye transfer inhibiting properties while not adversely affecting the cleaning performance of detergent compositions formulated therewith.

The N-vinylimidazole N-vinylpyrrolidone copolymer of the present invention has a molar ratio of N-vinylimidazole to N-vinylpyrrolidone from 1 to 0.2, more preferably from 0.8 to 0.3, most preferably from 0.6 to 0.4.

The detergent compositions of the present invention may also utilize polyvinylpyrrolidone ("PVP") having an average molecular weight of from about 2,500 to about 400,000, preferably from about 5,000 to about 200,000, more preferably from about 5,000 to about 50,000, and most preferably from about 5,000 to about 15,000. Suitable polyvinylpyrrolidones are commercially vailable from ISP Corporation, New York, N.Y. and Montreal, Canada under the product names PVP K-15 (viscosity molecular weight of 10,000), PVP K-30 (average molecular weight of 40,000), PVP K-60 (average molecular weight of 160,000), and PVP K-90 (average molecular weight of 360,000). Other suitable polyvinylpyrrolidones which are commercially available from BASF Cooperation include Sokalan HP 165 and Sokalan HP 12; polyvinylpyrrolidones known to persons skilled in the detergent field (see for example EP-A-262,897 and EP-A-256,696).

The detergent compositions of the present invention may also utilize polyvinyloxazolidone as a polymeric dye transfer inhibiting agent. Said polyvinyloxazolidones have an average molecular weight of from about 2,500 to about 400,000, preferably from about 5,000 to about 200,000, more preferably from about 5,000 to about 50,000, and most preferably from about 5,000 to about 15,000.

The detergent compositions of the present invention may also utilize polyvinylimidazole as polymeric dye transfer inhibiting agent. Said polyvinylimidazoles have an average about 2,500 to about 400,000, preferably from about 5,000 to about 200,000, more preferably from about 5,000 to about 50,000, and most preferably from about 5,000 to about 15,000.

Method of Washing

The process described herein comprises contacting fabrics with a laundering solution in the usual manner and exemplified hereunder.

The process of the invention is conveniently carried out in the course of the cleaning process. The method of cleaning is preferably carried out at 5° C. to 95 ° C., especially between 10° C. and 60° C. The pH of the treatment solution is preferably from 7 to 11, especially from 7.5 to 10.5.

The following examples are meant to exemplify compositions of the present invention, but are not necessarily meant to limit or otherwise define the scope of the invention.

In the detergent compositions, the abbreviated component identifications have the following meanings:

LAS: Sodium linear $C_{12}$ alkyl benzene sulphonate

TAS: Sodium tallow alkyl sulphate

XYAS: Sodium $C_{1X}$–$C_{1Y}$ alkyl sulfate

SAS: $C_{12}$–$C_{14}$ secondary (2,3) alkyl sulfate in the form of the sodium salt.

APG: Alkyl polyglycoside surfactant of formula $C_{12}$–(glycosyl)$_x$, where x is 1.5.

AEC: Alkyl ethoxycarboxylate surfactant of formula $C_{12}$ ethoxy (2) carboxylate.

SS: Secondary soap surfactant of formula 2-butyl octanoic acid

25EY: A $C_{12}$–$C_{15}$ predominantly linear primary alcohol condensed with an average of Y moles of ethylene oxide 45EY: A $C_{14}$–$C_{15}$ predominantly linear primary alcohol condensed with an average of Y moles of ethylene oxide XYEZS: $C_{1X}$–$C_{1Y}$ sodium alkyl sulfate condensed with an average of Z moles of ethylene oxide per mole Nonionic: $C_{13}$–$C_{15}$ mixed ethoxylated/propoxylated fatty alcohol with an average degree of ethoxylation of 3.8 and an average degree of propoxylation of 4.5 sold under the tradename Plurafax LF404 by BASF Gmbh CFAA: $C_{12}$–$C_{14}$ alkyl N-methyl glucamide TFAA: $C_{16}$–$C_{18}$ alkyl N-methyl glucamide.

Silicate: Amorphous Sodium Silicate ($SiO_2$:$Na_2O$ ratio=2.0)

NaSKS-6: Crystalline layered silicate of formula δ-$Na_2Si_2O_5$

Cabonate: Anhydrous sodium carbonate

Phosphate: Sodium tripolyphosphate

MA/AA: Copolymer of 1:4 maleic/acrylic acid, average molecular weight about 80,000

Polyacrylate: Polyacrylate homopolymer with an average molecular weight of 8,000 sold under the tradename PA30 by BASF GmbH Zeolite A: Hydrated Sodium Aluminosilicate of formula $Na_{12}(AlO_2SiO_2)_{12}.27H_2O$ having a primary particle size in the range from 1 to 10 micrometers Citrate: Tri-sodium citrate dihydrate Citric: Citric Acid Perborate: Anhydrous sodium perborate monohydrate bleach, empirical formula $NaBO_2.H_2O_2$ PB4: Anhydrous sodium perborate tetrahydrate Percarbonate: Anhydrous sodium percarbonate bleach of empirical formula $2Na_2CO_3.3H_2O_2$ TAED: Tetraacetyl ethylene diamine Paraffin: Paraffin oil sold under the tradename Winog 70 by Wintershall.

Xylanase: Xylanolytic enzyme sold under the tradenames Pulpzyme HB or SP431 by Novo Nordisk A/S or Lyxasan (Gist-Brocades) or Optipulp or Xylanase (Solvay).

Protease: Proteolytic enzyme sold under the tradename Savinase by Novo Nordisk A/S. Protease D: Proteolytic enzyme which is a *Bacillus lentus* subtilisin variant N76D/S103 A/V1041, according to the numbering of *Bacillus amyloliquefaciens* subtilisin.

Amylase: Amylolytic enzyme sold under the tradename Termamyl by Novo Nordisk A/S Lipase: Lipolytic enzyme sold under the tradename Lipolase by Novo Nordisk A/S D96Lipase: Variant of the native lipase derived from *Humicola lanuginosa*

Peroxidase: Peroxidase enzyme

Cellulase: Cellulosic enzyme sold under the tradename Carezyme or Celluzyme by Novo Nordisk A/S.

CMC: Sodium carboxymethyl cellulose

HEDP: 1,1-hydroxyethane diphosphonic acid

DETPMP: Diethylene triamine penta (methylene phosphonic acid), marketed by Monsanto under the Trade name Dequest 2060

PVP: Polyvinyl pyrrolidone polymer

EDDS: Ethylenediamine -N, N'- disuccinic acid, [S,S] isomer in the form of the sodium salt.

Suds Suppressor: 25% paraffin wax Mpt 50° C., 17% hydrophobic silica, 58% paraffin oil.

Granular Suds Suppressor: 12% Silicone/silica, 18% stearyl alcohol, 70% starch in granular form SCS: Sodium cumene sulphonate Sulphate: Anhydrous sodium sulphate.

HMWPEO: High molecular weight polyethylene oxide

PGMS: Polyglycerol monostearate having a tradename of Radiasuff248

TAE 25: Tallow alcohol ethoxylate (25)

In the following examples all levels of enzyme quoted are expressed as % active enzyme by weight of the composition:

EXAMPLE 1

A compact granular fabric cleaning composition in accord with the invention is prepared as follows:

| | |
|---|---|
| 45AS | 9.0 |
| 25E3S | 2.3 |
| 25E5 | 4.4 |
| TFAA | 1.9 |
| Zeolite A | 14.1 |
| NaSKS-6 | 11.9 |
| Citric acid | 3.2 |
| Carbonate | 7.1 |
| MA/AA | 4.5 |
| CMC | 0.4 |
| Poly(4-vinylpyridine)-N-oxide/ copolymer of vinylimidazole and vinylpyrrolidone | 0.027 |
| D96L Lipase | To provide 5000 LU/L wash |
| Protease | 0.03 |
| Cellulase | 0.0006 |
| Amylase | 0.006 |
| TAED | 4.9 |
| Percarbonate | 22.3 |
| Granular suds suppressor | 3.6 |
| water/minors | Up to 100% |

Use of this laundry detergent composition to wash fabrics identified by consumers as having dingy soil buildup results in improved dingy clean-up of these fabrics versus the dingy clean-up achieved using this composition comprising only D96L Lipase or Protease.

EXAMPLE 2

A granular fabric cleaning composition in accord with the invention is prepared as follows:

| | |
|---|---|
| LAS | 10.3 |
| 45AS | 6.6 |
| 25AE3S | 1.8 |
| Zeolite A | 26.3 |
| Carbonate | 26.3 |
| PEG | 1.7 |
| Polyacrylate | 3.2 |
| Na2SO4 | 10.3 |
| 23E6.5 | 0.5 |
| D96L Lipase | To provide 300 LU/L wash |
| Protease D | To provide 0.1 mg active protease/L wash |
| Water and minors | up to 100% |

Use of this laundry detergent composition to wash fabrics identified by consumers as having dingy soil buildup results in improved dingy clean-up of these fabrics versus the dingy clean-up achieved using this composition comprising only D96L Lipase or Protease D.

Similar results can be observed substituting into this formula Lipase for the D96L Lipolase, or by using both Lipase and D96L Lipase; and by substituting Protease, Maxacal®, Protease A, Protease B, or Protease C, or mixtures thereof with Protease D.

EXAMPLE 3

Granular fabric cleaning compositions in accord with the invention are prepared as follows:

|  | I | II | III | IV |
|---|---|---|---|---|
| LAS | 22.0 | 22.0 | 22.0 | 22.0 |
| Phosphate | 23.0 | 23.0 | 23.0 | 23.0 |
| Carbonate | 23.0 | 23.0 | 23.0 | 23.0 |
| Silicate | 14.0 | 14.0 | 14.0 | 14.0 |
| Zeolite A | 8.2 | 8.2 | 8.2 | 8.2 |
| DETPMP | 0.4 | 0.4 | 0.4 | 0.4 |
| Sodium Sulfate | 5.5 | 5.5 | 5.5 | 5.5 |
| Protease | 0.01 | — | 0.01 | 0.005 |
| Protease D | — | 0.02 | 0.01 | — |
| Xylanase | 0.04 | — | — | — |
| D96L Lipase | 0.005 | — | 0.002 | 0.005 |
| Lipase | — | 0.005 | — | — |
| Cellulase | 0.001 | — | — | 0.001 |
| Amylase | 0.01 | — | 0.01 | — |
| Pectinase | 0.02 | — | — | — |
| Water/minors | Up to 100% | | | |

EXAMPLE 4

Granular fabric cleaning compositions in accord with the invention are prepared as follows:

|  | I | II | III | IV |
|---|---|---|---|---|
| LAS | 12.0 | 12.0 | 12.0 | 12.0 |
| Zeolite A | 26.0 | 26.0 | 26.0 | 26.0 |
| SS | 4.0 | 4.0 | 4.0 | 4.0 |
| SAS | 5.0 | 5.0 | 5.0 | 5.0 |
| Citrate | 5.0 | 5.0 | 5.0 | 5.0 |
| Sodium Sulfate | 17.0 | 17.0 | 17.0 | 28.0 |
| Perborate | 16.0 | 16.0 | 16.0 | — |
| TAED | 5.0 | 5.0 | 5.0 | — |
| Xylanase | 0.20 | — | — | — |
| Protease | 0.06 | — | 0.02 | 0.08 |
| Protease D | — | 0.03 | 0.01 | — |
| D96L Lipase | 0.005 | 0.0003 | 0.01 | 0.005 |
| Cellulase | 0.001 | — | — | 0.001 |
| Amylase | 0.01 | — | 0.01 | — |
| Pectinase | 0.02 | — | — | — |
| Water/minors | Up to 100% | | | |

EXAMPLE 5

Granular fabric cleaning compositions in accord with the invention which are especially useful in the laundering of coloured fabrics are prepared as follows:

| LAS | 11.4 | 10.7 | — |
|---|---|---|---|
| TAS | 1.8 | 2.4 | — |
| TFAA | — | — | 4.0 |
| 45AS | 3.0 | 3.1 | 10.0 |
| 45E7 | 4.0 | 4.0 | — |
| 25E3S | — | — | 3.0 |
| 68E11 | 1.8 | 1.8 | — |
| 25E5 | — | — | 8.0 |
| Citrate | 14.0 | 15.0 | 7.0 |
| Carbonate | — | — | 10 |
| Citric acid | 3.0 | 2.5 | 3.0 |
| Zeolite A | 32.5 | 32.1 | 25.0 |
| Na-SKS-6 | — | — | 9.0 |
| MA/AA | 5.0 | 5.0 | 5.0 |
| DETPMP | 1.0 | 0.2 | 0.8 |
| Xylase | 0.01 | — | — |
| Protease | 0.02 | — | 0.01 |
| Protease D | — | 0.02 | — |
| D96L Lipase | 0.0005 | 0.01 | 0.005 |
| Amylase | 0.03 | 0.03 | 0.005 |
| Pectinase | 0.01 | — | — |
| Cellulase | 0.005 | — | 0.001 |
| Silicate | 2.0 | 2.5 | — |
| Sulphate | 3.5 | 5.2 | 3.0 |
| PVP | 0.3 | 0.5 | — |
| Poly(4-vinylpyridine)-N-oxide/ copolymer of vinyl-imidazole and vinyl-pyrrolidone | — | — | 0.2 |
| Perborate | 0.5 | 1.0 | — |
| Peroxidase | 0.01 | 0.01 | — |
| Phenol sulfonate | 0.1 | 0.2 | — |
| Water/Minors | Up to 100% | | |

EXAMPLE 6

Granular fabric cleaning compositions in accord with the invention are prepared as follows:

| LAS | 6.5 | 8.0 |
|---|---|---|
| Sulfate | 15.0 | 18.0 |
| Zeolite A | 26.0 | 22.0 |
| Sodium nitrilotriacetate | 5.0 | 5.0 |
| PVP | 0.5 | 0.7 |
| TAED | 3.0 | 3.0 |
| Boric acid | 4.0 | — |
| Perborate | 0.5 | 1.0 |
| Phenol sulphonate | 0.1 | — |
| Protease D | 0.06 | 0.02 |
| Xylanase | 0.01 | — |
| Silicate | 5.0 | 5.0 |
| Carbonate | 15.0 | 15.0 |
| Peroxidase | 0.1 | — |
| D96L Lipase | 0.001 | 0.0005 |
| Amylase | 0.01 | 0.01 |
| Pectinase | 0.02 | — |
| Cellulase | 0.005 | 0.002 |
| Water/minors | Up to 100% | |

EXAMPLE 7

A granular fabric cleaning compositions in accord with the invention which provide "softening through the wash" capability are prepared as follows:

| 45AS | — | 10.0 |
|---|---|---|
| LAS | 7.6 | — |
| 68AS | 1.3 | — |
| 45E7 | 4.0 | — |
| 25E3 | — | 5.0 |
| Coco-alkyl-dimethyl hydroxy-ethyl ammonium chloride | 1.4 | 1.0 |
| Citrate | 5.0 | 3.0 |
| Na-SKS-6 | — | 11.0 |
| Zeolite A | 15.0 | 15.0 |
| MA/AA | 4.0 | 4.0 |
| DETPMP | 0.4 | 0.4 |
| Perborate | 15.0 | — |
| Percarbonate | — | 15.0 |
| TAED | 5.0 | 5.0 |
| Smectite clay | 10.0 | 10.0 |
| HMWPEO | — | 0.1 |
| Protease | 0.02 | 0.01 |
| D96L Lipase | 0.002 | 0.0003 |
| Amylase | 0.03 | 0.005 |
| Xylanase | 0.03 | — |
| Cellulase | 0.02 | 0.001 |
| Pectinase | 0.01 | — |
| Silicate | 3.0 | 5.0 |
| Carbonate | 10.0 | 10.0 |
| Granular suds suppressor | 1.0 | 4.0 |
| CMC | 0.2 | 0.1 |
| Water/minors | Up to 100% | |

EXAMPLE 8

Heavy duty liquid fabric cleaning compositions suitable for use in the pretreatment of stained fabrics, and for use in a machine laundering method, in accord with the invention are prepared as follows:

| | I | II | III | IV | V |
|---|---|---|---|---|---|
| 24AS | 20.0 | 20.0 | 20.0 | 20.0 | 20.0 |
| SS | 5.0 | 5.0 | 5.0 | 5.0 | 5.0 |
| Citrate | 1.0 | 1.0 | 1.0 | 1.0 | 1.0 |
| 12E$_3$ | 13.0 | 13.0 | 13.0 | 13.0 | 13.0 |
| Monethanolamine | 2.5 | 2.5 | 2.5 | 2.5 | 2.5 |
| Xylanase | 0.02 | — | — | — | — |
| Protease | 0.005 | 0.03 | 0.02 | 0.04 | 0.01 |
| D96L Lipase | 0.002 | 0.01 | 0.0005 | 0.001 | 0.004 |
| Amylase | 0.005 | 0.005 | — | — | 0.004 |
| Cellulase | 0.04 | — | 0.01 | — | — |
| Pectinase | 0.02 | 0.02 | — | — | — |
| Water/propylene glycol/ethanol (100:1:1) | | | | | |

EXAMPLE 9

Heavy duty liquid fabric cleaning compositions in accord with the invention are prepared as follows:

| | I | II | III | IV |
|---|---|---|---|---|
| LAS acid form | — | — | 25.0 | — |
| C$_{12-14}$ alkenyl succinic acid | 3.0 | 8.0 | 10.0 | — |
| Citric acid | 10.0 | 15.0 | 2.0 | 2.0 |
| 25AS acid form | 8.0 | 8.0 | — | 15.0 |
| 25AE2S acid form | — | 3.0 | — | 4.0 |
| 25AE7 | — | 8.0 | — | 6.0 |
| 25AE3 | 8.0 | — | — | — |
| CFAA | — | — | — | 6.0 |
| DETPMP | 0.2 | — | 1.0 | 1.0 |
| Fatty acid | — | — | — | 10.0 |
| Oleic acid | 1.8 | — | 1.0 | — |
| Ethanol | 4.0 | 4.0 | 6.0 | 2.0 |
| Propanediol | 2.0 | 2.0 | 6.0 | 10.0 |
| Xylanase | 0.05 | — | — | — |
| Protease D | 0.02 | 0.02 | 0.02 | 0.01 |
| Amylase | 0.005 | 0.01 | 0.005 | 0.01 |
| D96L Lipase | 0.005 | 0.02 | 0.005 | 0.01 |
| Cellulase | 0.005 | — | — | — |
| Pectinase | 0.02 | — | — | — |
| Coco-alkyl dimethyl hydroxy ethyl ammonium chloride | — | — | 3.0 | — |
| Smectite clay | — | — | 5.0 | — |
| PVP | 1.0 | 2.0 | — | — |
| Perborate | — | 1.0 | — | — |
| Phenol sulphonate | — | 0.2 | — | — |
| Peroxidase | — | 0.01 | — | — |
| NaOH | Up to pH 7.5 | | | |
| Waters/minors | Up to 100% | | | |

What is claimed is:

1. A laundry detergent composition comprising:
   (a) from about 0.001% to about 2% of a lipase enzyme variant D96L of the native lipase derived from *Humicola lanuginosa* strain D SM 4106;
   (b) a protease enzyme selected from the group consisting of the *Bacillus lentus* subtilisin variant N76D/S103A/V104I according to the numbering of *Bacillus amyloliquefaciens* subtilisin at a level to provide from 0.005 to 0.1 AU per gram of composition; and
   (c) from about 0.1% to about 60% of a surfactant;
and wherein further said compositions comprise levels of lipase enzyme and protease enzyme such that the whitening performance of said compositions is increased.

2. A method for laundering fabrics to maintain whiteness and provide dingy cleanup, said method comprising contacting fabrics in need of whiteness and dingy clean-up with an aqueous solution comprising the laundry detergent composition according to claim 1, said aqueous solution comprising the lipase enzyme at a level of from about 150 to about 5000 LU per liter.

* * * * *